(12) United States Patent
Teng

(10) Patent No.: US 7,837,468 B2
(45) Date of Patent: Nov. 23, 2010

(54) LONG-ARM TYPE UPRIGHT MOLAR TOOTH SPRING

(76) Inventor: Chi-Ming Teng, 3F.-7, No.357, Sec. 4, Sinyi Rd., Sinyi District, Taipei (TW) 110

( * ) Notice: Subject to any disclaimer, the term of this patent is extended or adjusted under 35 U.S.C. 154(b) by 199 days.

(21) Appl. No.: 12/022,894

(22) Filed: Jan. 30, 2008

(65) Prior Publication Data
US 2009/0191501 A1  Jul. 30, 2009

(51) Int. Cl.
*A61C 3/00* (2006.01)
(52) U.S. Cl. ........................................................ 433/21
(58) Field of Classification Search ................... 433/18, 433/21, 149, 24
See application file for complete search history.

(56) References Cited

U.S. PATENT DOCUMENTS

| | | | | |
|---|---|---|---|---|
| 4,256,456 A | * | 3/1981 | Wallshein | 433/21 |
| 5,199,869 A | * | 4/1993 | McGann | 433/21 |
| 5,314,331 A | * | 5/1994 | Brosius et al. | 433/21 |
| 5,720,611 A | | 2/1998 | Teng | |
| 2004/0197726 A1 | * | 10/2004 | Miyawaki et al. | 433/21 |
| 2007/0184400 A1 | * | 8/2007 | White | 433/21 |

* cited by examiner

*Primary Examiner*—Cris L Rodriguez
*Assistant Examiner*—Edward Moran
(74) *Attorney, Agent, or Firm*—WPAT, PC; Justin King

(57) ABSTRACT

A long-arm type upright molar tooth spring includes a lingual groove rest, for resting the spring at a lingual groove of a first molar tooth; a loop, for surrounding and fixing the periphery of the second molar tooth; a buccal bracket rest, for resting the spring at a buccal bracket of the first molar tooth; a reactivating area, being an area between the first molar tooth and the second premolar tooth; a lever, for applying a force onto the second molar tooth; and an arc, extended from an adjacent wall between an engaging surface of the first molar tooth and an engaging surface of the second molar tooth, and fixed at a root of the second molar tooth.

4 Claims, 15 Drawing Sheets

LONG-ARM TYPE UPRIGHT MOLAR TOOTH SPRING

FIELD OF THE INVENTION

The present invention relates to a long-arm type upright molar tooth spring, and more particularly to a long-arm type upright molar tooth spring that uses the lever principle for a quick formation and saves time and material consumption.

BACKGROUND OF THE INVENTION

According to statistics, a misplaced impaction of the first molar tooth of the upper jaw and an impaction of the second molar tooth of the lower jaw occur in approximately 3% of the world's population. When a patient receives a correction treatment, the first molar tooth of the patient's lower jaw may incline backward due to an anchorage preparation, the problem of the tooth itself, or an insufficient arch length, such that the second molar tooth may be misplaced or impacted.

In general, a traditional way of treating an inclined molar tooth uses a brass wire to shift the first molar tooth towards a distal side (which is a rear end of the tooth socket) or an elevator to upright a molar tooth, if the situation is not too serious. As dental technologies advance, steel wire or band is used for uprighting and correcting a molar tooth.

Clinically, it is common to see an eruptive and impacted first molar tooth, which causes damages to periodontal tissues, decays to teeth, and adverse effects on the integrity of a dental arch. Since it is not easy to keep the area of the first molar tooth dry, the correction rest may be stuck, and thus making the installation of the correction band difficult.

In view of the foregoing shortcomings of the prior art, the inventor of the present invention has developed a long-arm type upright molar tooth spring made of a simple circular stainless steel wire, and adopting a first type of the principle of lever to overcome the difficulty of keeping the first molar tooth dry and prevent the correction rest from getting stuck. In clinical practices, we can see significant uprighting effects within two to five weeks depending on the inclination of the molar tooth, and the related technology has been disclosed in details in U.S. Pat. No. 5,720,611.

However, it will be easy to hurt a patient's tissues during the process of wearing the steel wire according to the aforementioned patent, if a dentist is not experienced. Obviously, such patented invention requires further improvements.

The inventor of the present invention further developed an improved long-arm type upright molar tooth spring extended into and fixed to an adjacent side between engaging surfaces of a normal tooth and an inclined tooth for uprighting the inclined tooth.

SUMMARY OF THE INVENTION

Therefore, it is a primary objective of the present invention to overcome the shortcomings of the prior art by providing a long-arm type upright molar tooth spring that is extended into and fixed to an adjacent side between engaging surfaces of a normal tooth and an inclined tooth for uprighting the inclined tooth.

To achieve the foregoing objective, the present invention provides a long-arm type upright molar tooth spring, comprising: a lingual groove rest, for resting the spring at a lingual groove of a first molar tooth; a loop, for surrounding and fixing the periphery of the second molar tooth; a buccal bracket rest, for resting the spring at a buccal bracket of the first molar tooth; a reactivating area, being an area between the first molar tooth and the second premolar tooth; a lever, for applying a force onto the second molar tooth; and an end arc, wherein the loop has a length spanning from the lingual groove of the first molar tooth to a marginal distance below the highest point of the profile of the mesial side of the impacted second molar tooth, and a width spanning from the lingual side of the first molar tooth to the buccal side of the first molar tooth, and includes a body having at least one contact end which extends to and directly contacts the wall of the impacted second molar tooth adjacent to the first molar tooth.

The above and other objects, features and advantages of the present invention will become apparent from the following detailed description taken with the accompanying drawing.

DESCRIPTION OF THE PREFERRED EMBODIMENT

Figure 1:
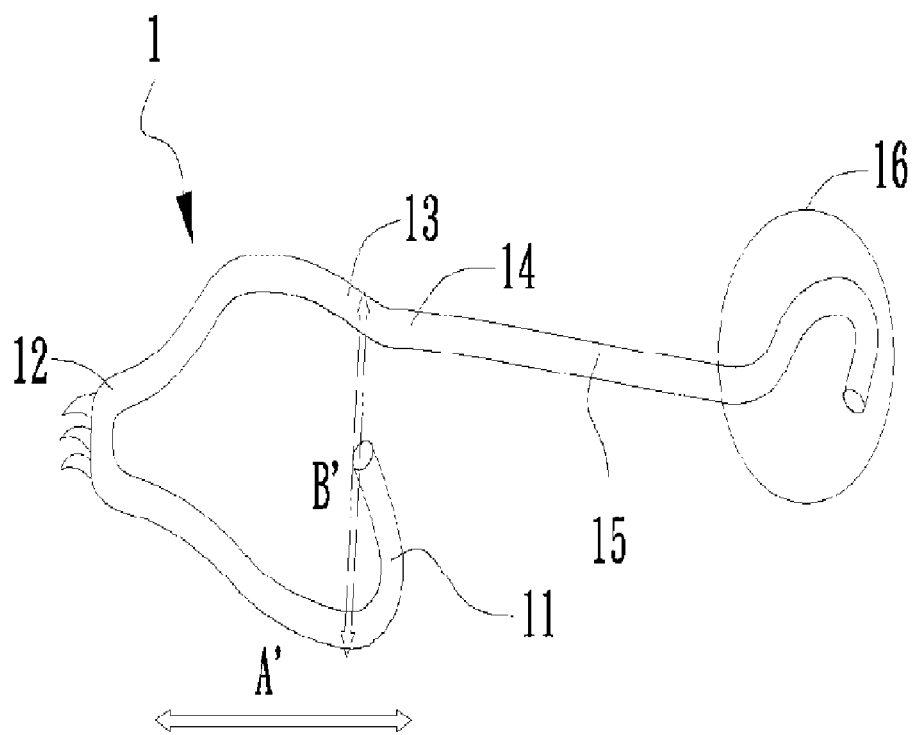
FIG. 1 shows a structural appearance of a long-arm type upright spring.

Referring to FIG. 1 for a schematic view of a long-arm type upright molar tooth spring of the present invention, the long-arm type upright molar tooth spring 1 is made of stainless steel 22 and may come with different specifications with a diameter of 0.018 inch, 0.020 inch or 0.022 inch. The long-arm type upright molar tooth spring 1 comprises: (A) a lingual groove rest 11, for resting the long-arm type upright molar tooth spring 1 at a lingual groove of a first molar tooth 31; (B) a loop 12 which includes a body which extends to and directly contacts the wall of the impacted second molar tooth adjacent to the first molar tooth, for surrounding and fixing the periphery of the second molar tooth 32; (C) a buccal bracket rest 13, for resting the long-arm type upright molar tooth spring 1 at a buccal bracket of the first molar tooth 31; (D) a reactivating area 14, being an area between the first molar tooth 31 and the second premolar tooth 34; (E) a lever 15, for applying a force on an impacted second molar tooth 32; and (F) an end arc 16.

The long-arm type upright molar tooth spring 1 of the invention uses the first lever principle to expose the impacted portion of the original molar tooth and disposed proximate to crown at the mesial side. With the correction conducted by the unique long-arm upright spring, a correct and appropriate clamp can be made according to the inclination of the molar tooth.

Figure 2A:
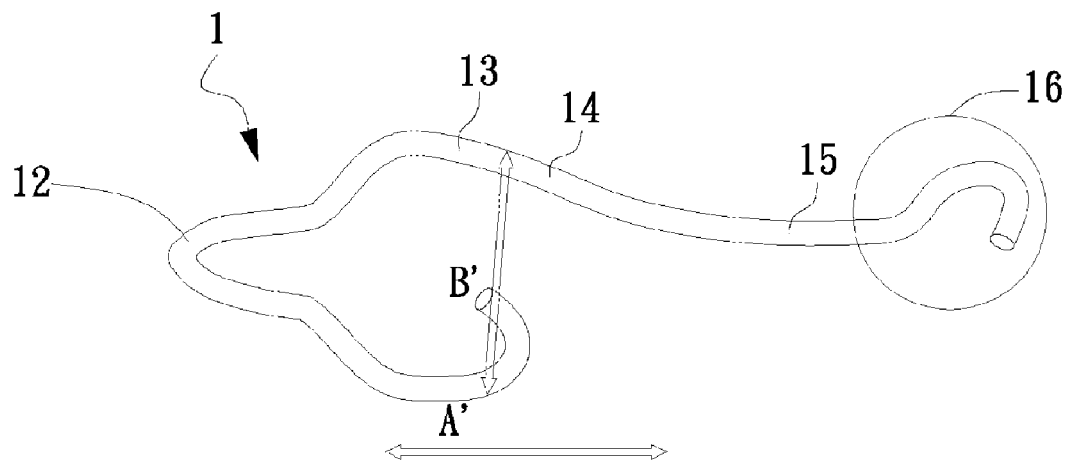
FIGS. 2A to 2D show different embodiments of a long-arm type upright spring.
Figure 2B:
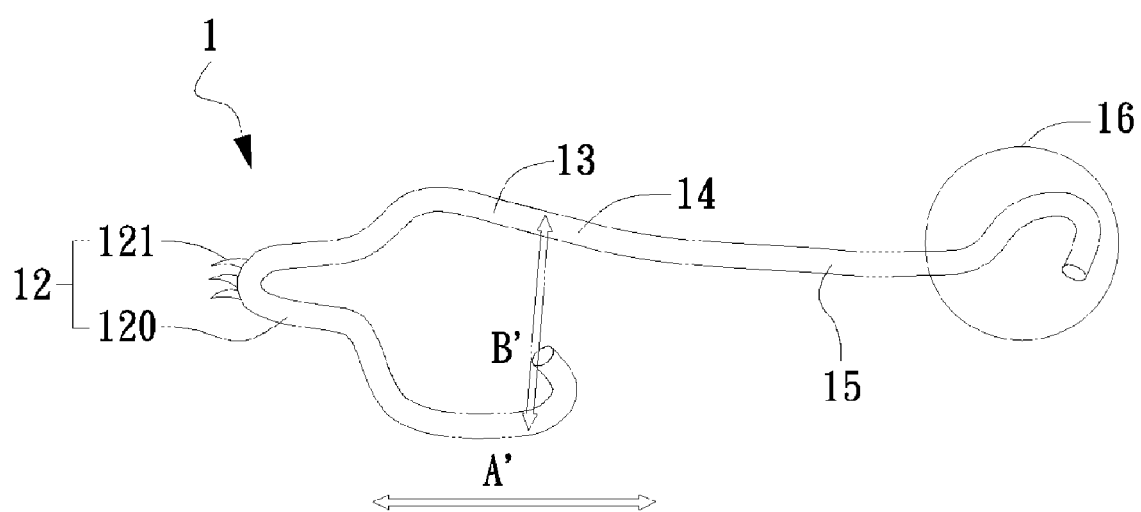
Figure 2C:
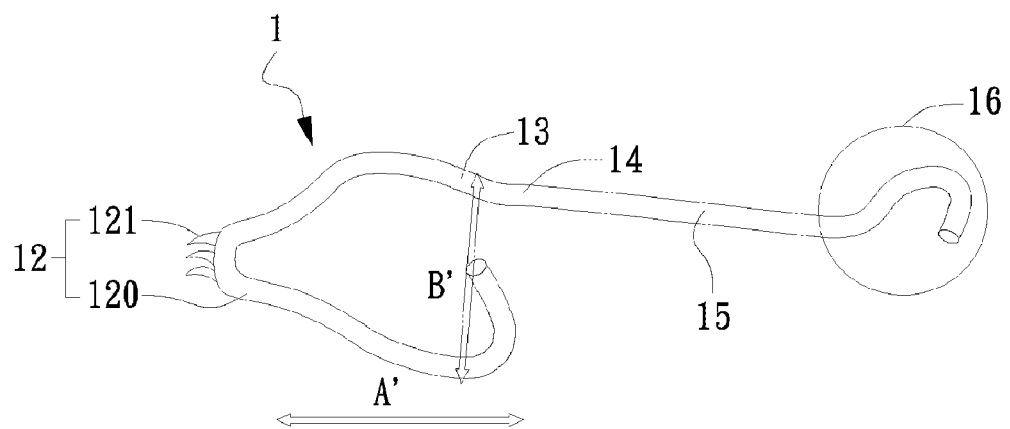
Figure 2D:
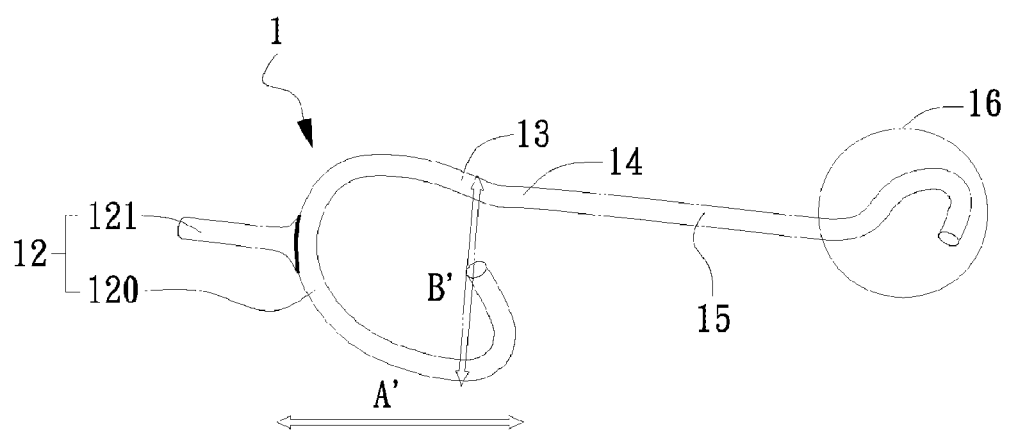

Referring to FIGS. 2A to 2D, the loop 12 can be in different forms. In the FIGS. 2A to 2C, the loop 12 comprises a U-shape body 120 including a first outward curve, an inward curve, and a second outward curve; and the FIGS. 2B and 2C further illustrates that the body further comprises a plurality of contact ends 121. In FIG. 2D, an embodiment shows that the body 120 has a single contact end attached on the body. The body 120 is inserted between an adjacent wall between an engaging surface of the first molar tooth 31 and an engaging surface of the second molar tooth 32 and is in contact with the root of the second molar tooth 32 by the contact end 121 when installed. The contact end 121 can be connected to the body 120, or integrally formed with the body 120 by molding.

Figure 3:
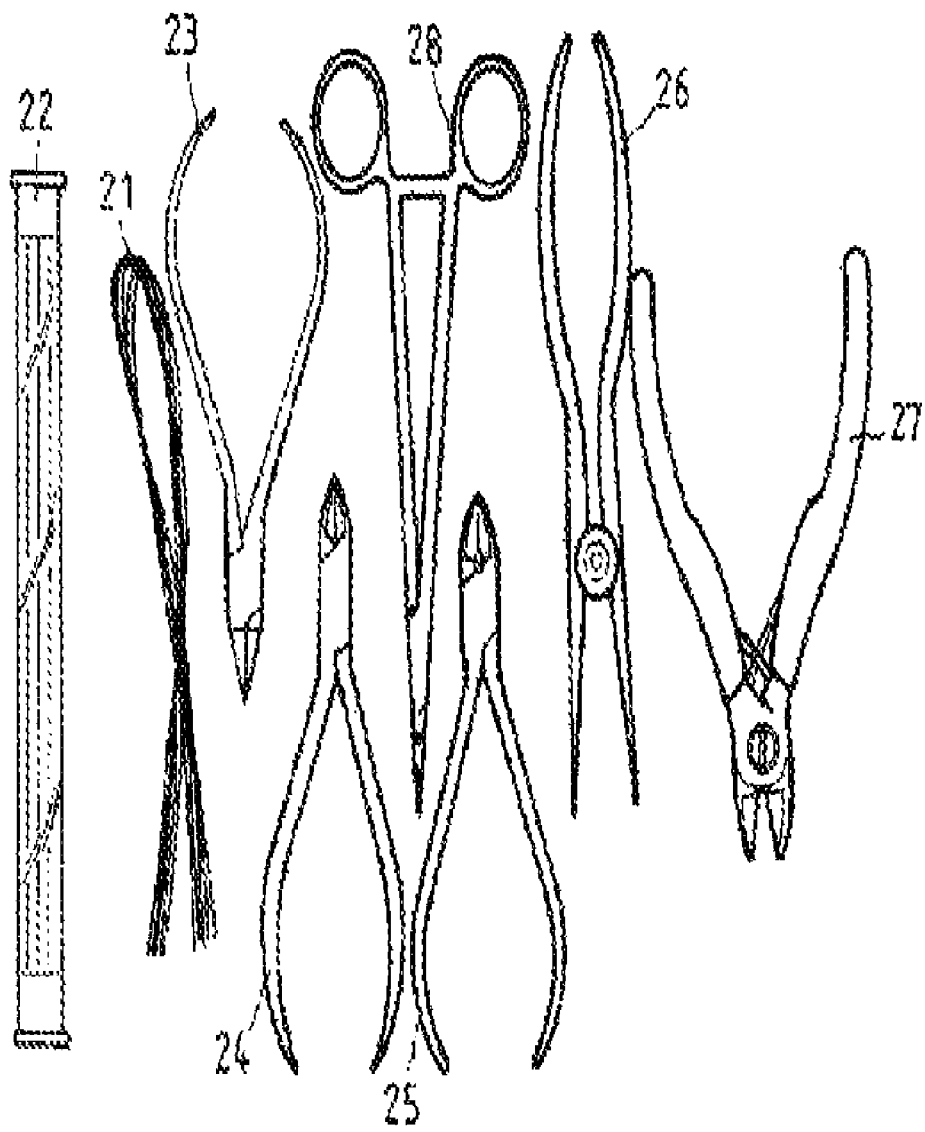
FIG. 3 shows different equipments and tools.

In this embodiment, the long-arm type upright spring 1 requires the following tools or equipments as shown in FIG. 3 for correcting an impacted molar tooth.

(1) a ligature wire 21;
(2) a stainless steel wire 220 of 018 inch, 0.020 inch or 0.022 inch long;
(3) a pair of loop contouring pliers 23;
(4) a pair of No. 139 correction pliers 24, 25;
(5) a ligature forceps 26;
(6) a cutting pliers 27; and
(7) a needle holder 28.

To make it easier for our examiner to understand each part of the whole structure and the operating procedure of the present invention in details, we use a preferred embodiment of a clinical correction procedure of uprighting a first molar tooth for illustrating the present invention as follows.

Figure 4:
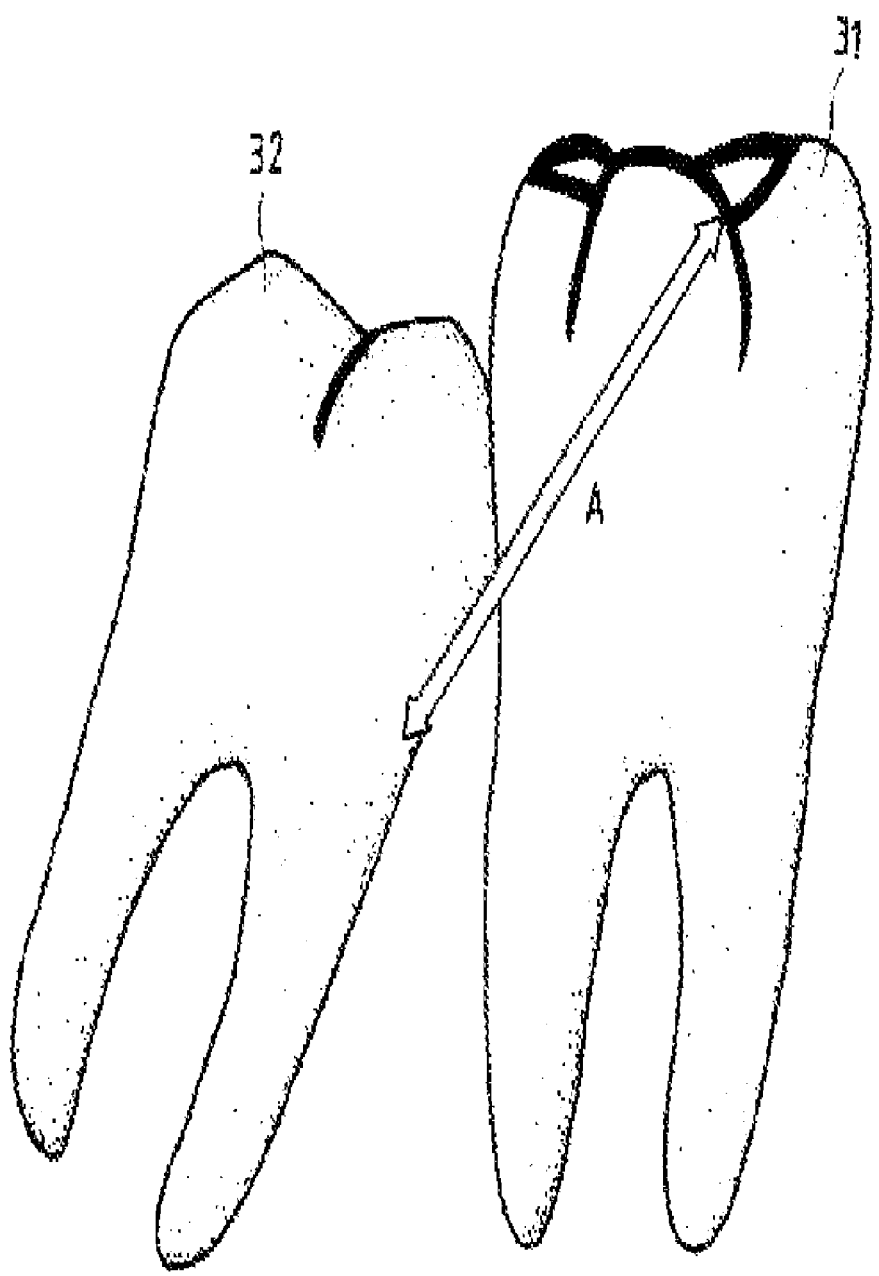
FIG. 4 is a side view of a portion of an impacted molar tooth.

(1) Measure the length A from the lingual groove of the first molar tooth 31 to 1 cm below the highest point of the profile of the mesial side of the impacted second molar tooth 32 (which is the front side of the tooth socket) from the X-ray film (as shown in FIG. 4).

Figure 5:
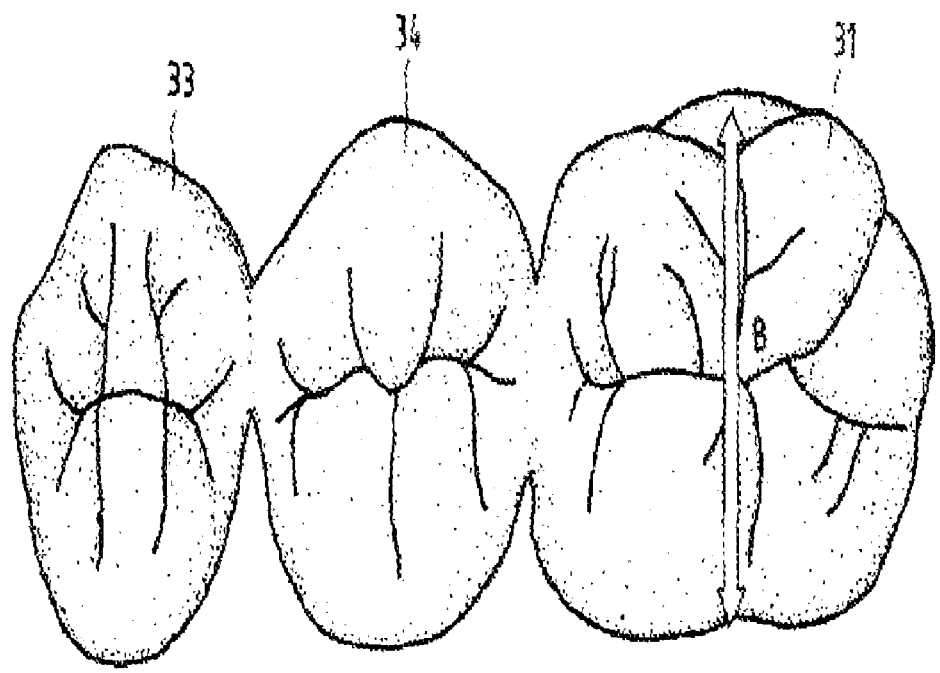
FIG. 5 is a top view of a first molar tooth.

(2) Measure the width B from the lingual side of the first molar tooth 31 to the buccal side (as shown in FIG. 5).

(3) Use a pair of No. 139 correction pliers to bend the steel wire into the shape as shown in FIG. 1, wherein A' indicates the distance between the mostly concave position of the lingual groove rest 11 and the mostly convex position of the loop 12, and B' indicates the distance from the starting end of the loop 12 to the buccal bracket rest 13, and the steel wire is formed, such that A=A' and B=B'. If A<A', the spring can be separated from the contact area in advance.

Figure 6:
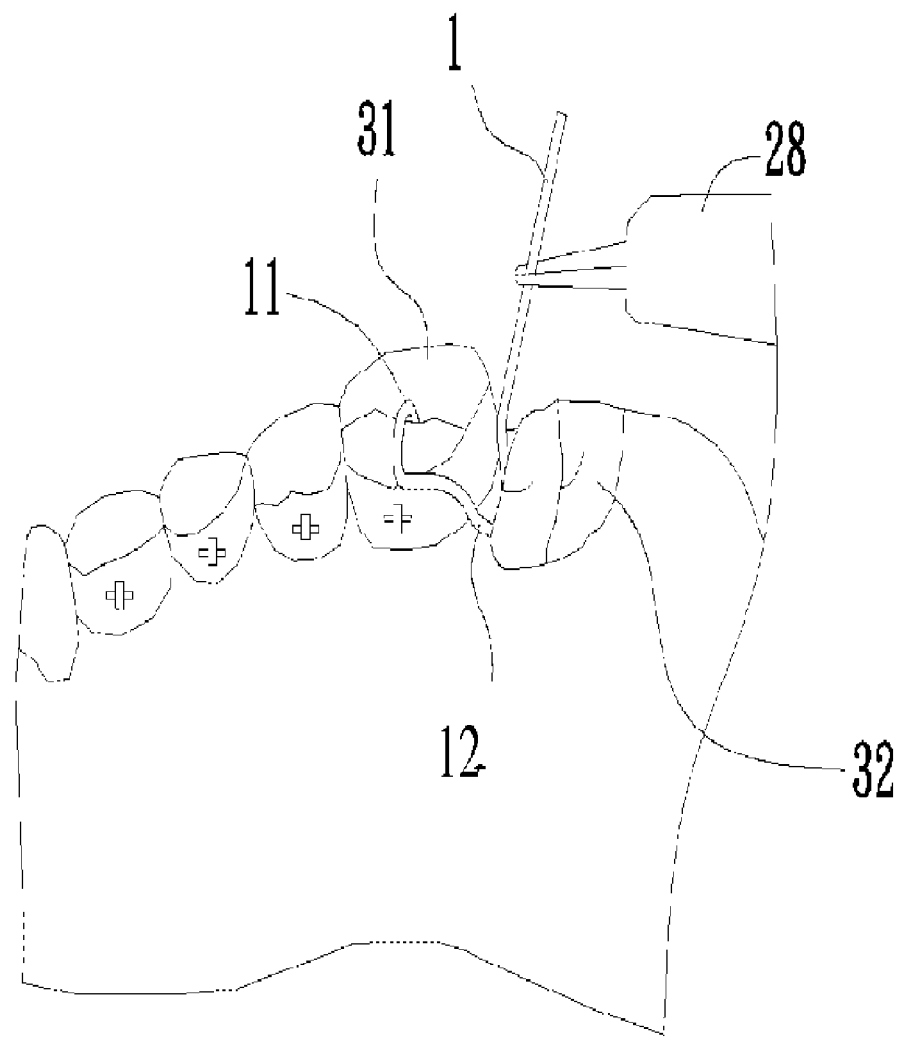
FIG. 6 is a schematic view of passing a needle holder from a lingual contact area to clamp the front end of an arc
Figure 7:
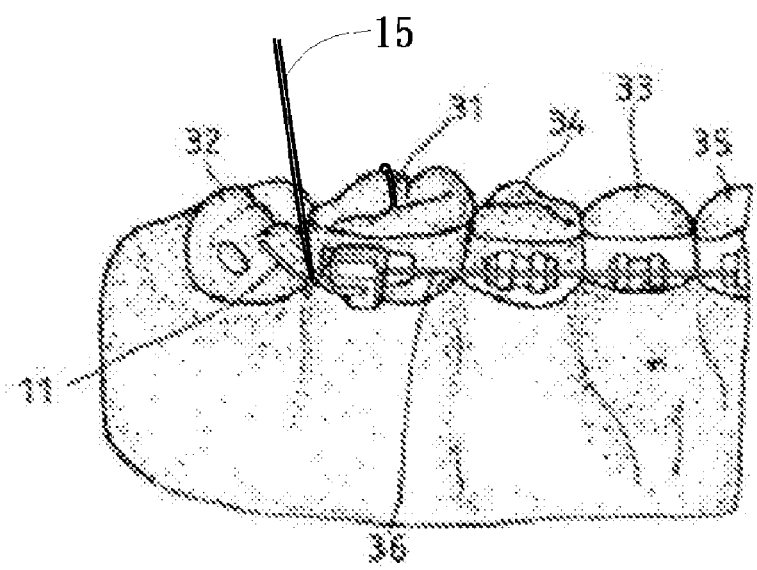
FIG. 7 is a schematic view of passing an upright spring out from a buccal side and using a pair of No. 139 correction pliers for a pull out.
Figure 8:
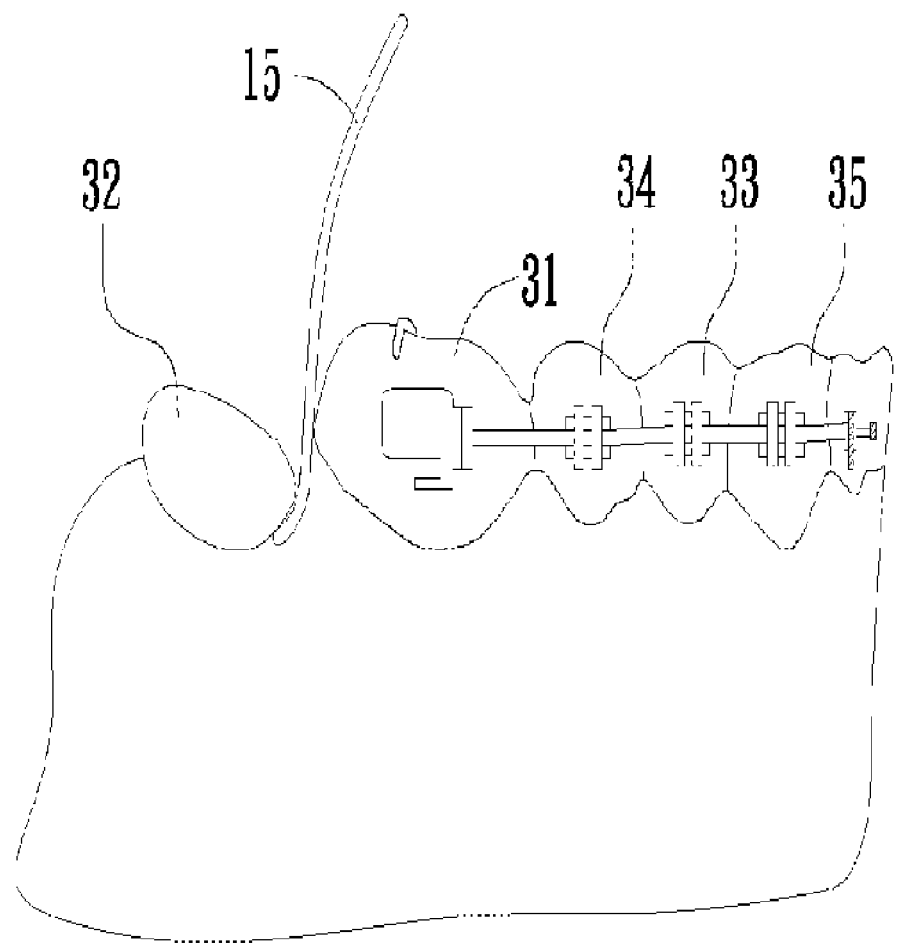
FIG. 8 is a schematic view of passing a lever from a buccal side.
Figure 9:
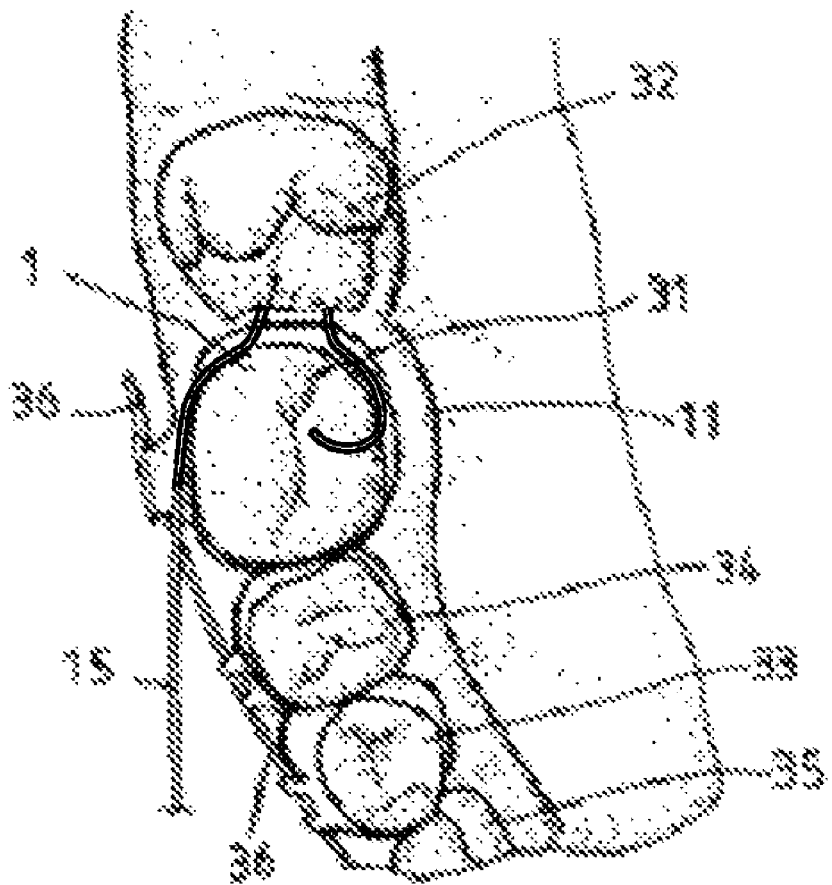
FIG. 9 is a schematic view of positioning a lingual groove rest.

(4) Use a needle holder to clamp the body 12 extended into the adjacent wall between an engaging side of the first molar tooth 31 and an engaging side of the impacted second molar tooth 32 (as shown in FIG. 6), and then the "lever" 15 is pulled out by the No. 139 correction pliers (as shown in FIGS. 7 and 8) and fixed at the root of the impacted second molar tooth 32, so that the lingual groove rest 11 of the long-arm type upright molar tooth spring is aligned precisely with the first molar tooth 31 (as shown in FIG. 9).

Figure 10:
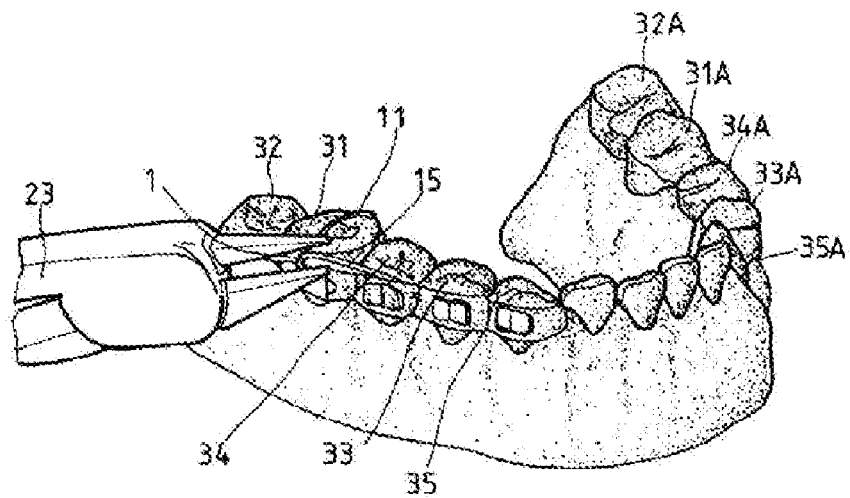
FIG. 10 is a schematic view of tying a lever to a canine and cutting away an excessive wire.

(5) Tie the lever 15 to the bracket of the canine 35 proximate to the gum, and cut away the extra steel wire (as shown in FIG. 10).

Figure 11:
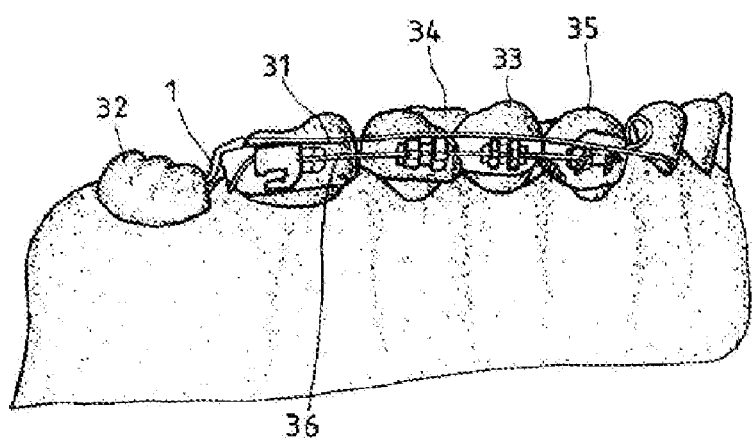
FIG. 11 shows a protruded area interfering an engagement.
Figure 12:
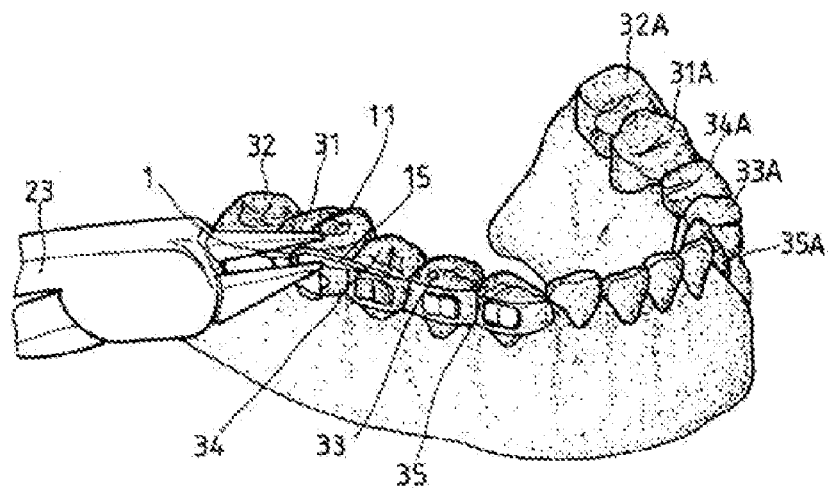
FIG. 12 shows a schematic view of using a pair of loop contouring pliers to remove a protruded area, and activating the upright spring.
Figure 13:
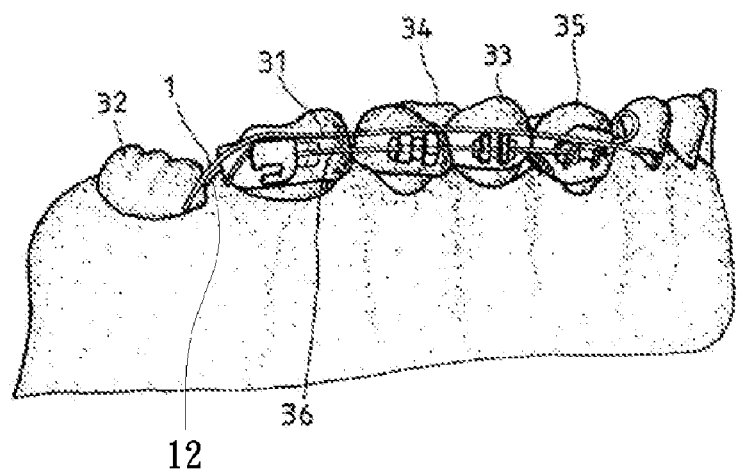
FIG. 13 shows the disappearance of a protruded area.
Figure 14:
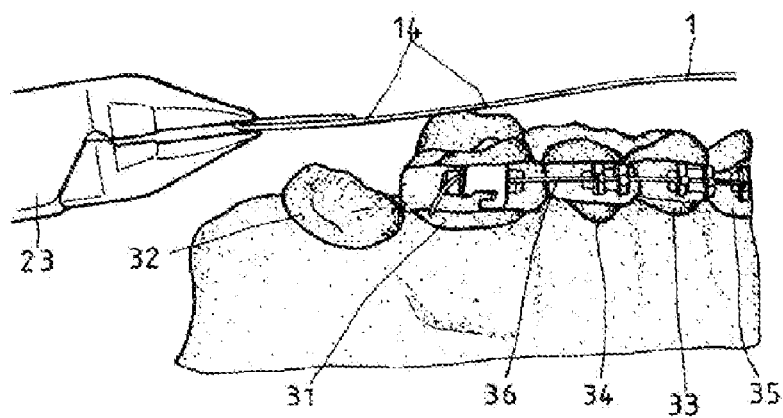
FIG. 14 shows a status before the activation.
Figure 15:
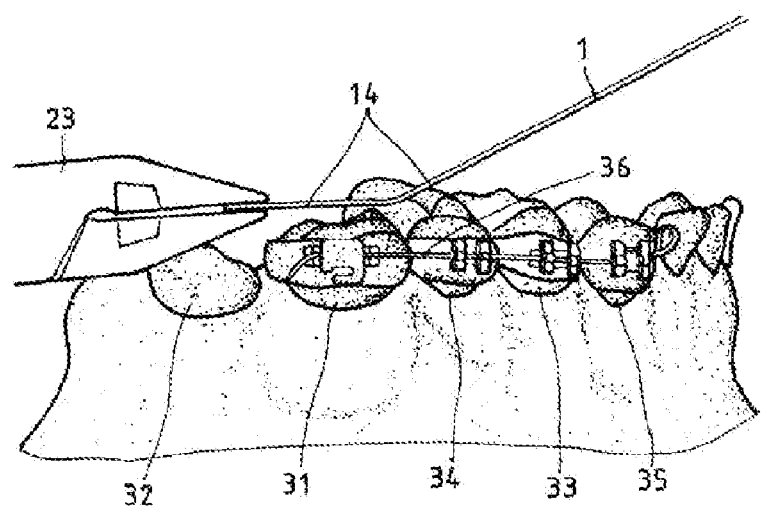
FIG. 15 shows a status after the activation.

(6) If a protruding area formed between the canine 35 and the first molar tooth 31 interferes the biting and makes it uncomfortable for the patient to bite, then a loop contouring pliers 23 can be used to improve the situation. In FIGS. 11 and 12, the way of removing the protruding area is illustrated. FIG. 13 shows that the protruding area of the long-arm type upright molar tooth spring disappears after the loop contouring pliers 23 are used. In the meantime, the force of the upright spring provides reinforcements through the reactivating area 14 according to the user's molar tooth uprighting requirements FIGS. 14 and 15 show the conditions before and after the reactivation respectively.

Figure 16:
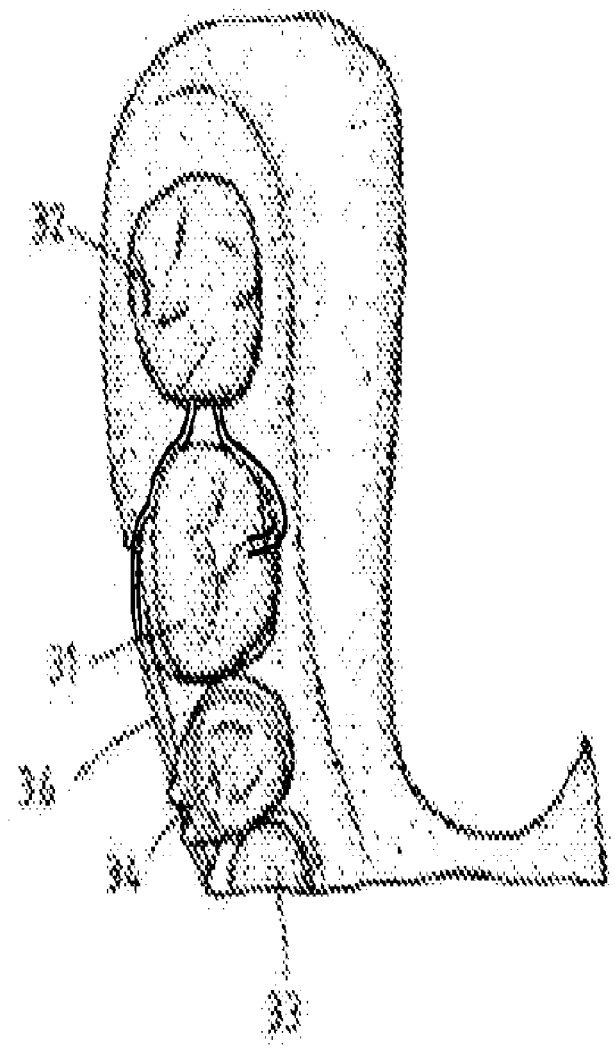
FIG. 16 shows the result of an uprighting molar tooth.
Figures 17A, 17B:
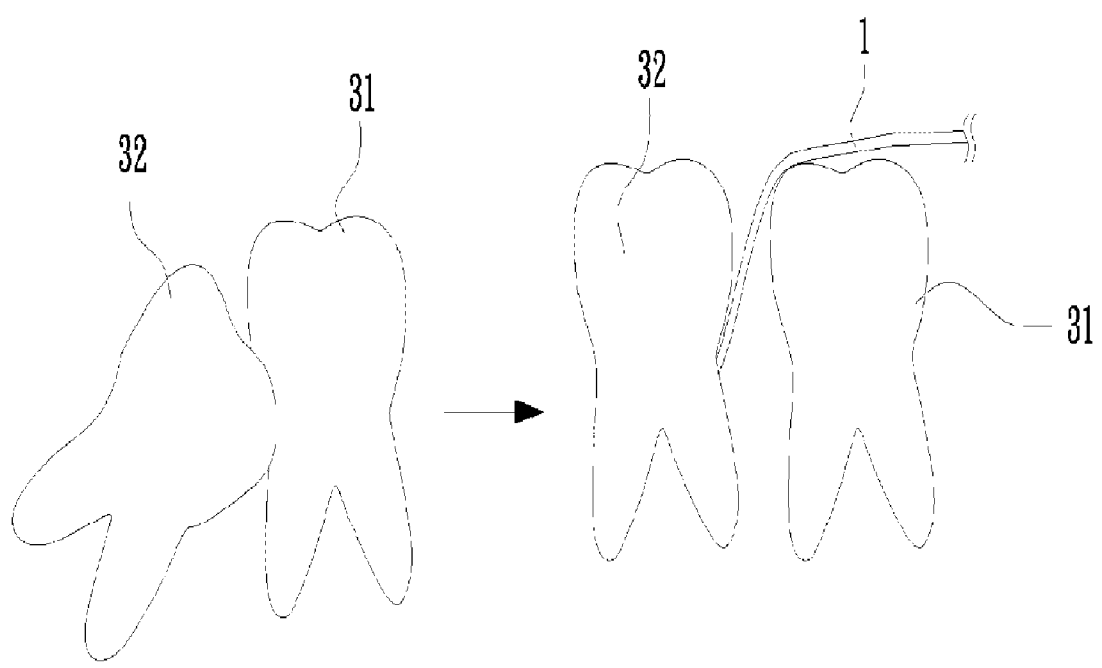
FIGS. 17A and 17B respectively show an impacted molar tooth before and after a treatment.

(7) With the correction procedure as described in the aforementioned steps (1) to (6), the patient's molar tooth can be corrected in a short time (approximately two to five weeks) with a satisfactory uprighting and correcting effect of the second molar tooth 32 (as shown in FIG. 16). FIG. 17A shows the arrangement of the molar tooth before the correction, and FIG. 17B shows the arrangement of the molar tooth after the correction, and a significant difference is shown before and after the correction, and thus the upright spring of the invention has a very good effect on correcting the molar tooth.

To reduce the side effect caused by the fixed pulling force of the upright spring 1 between the first molar tooth 31 and the bracket of the canine 35. The main wire is preferably a 0.018× 0.025 square wire for tying all brackets together to form a good anchorage preparation, and a correction band may be applied onto the upright tooth, and the angle of the correction band may be adjusted, so that a patient may be partially anesthetized for the first time of taking the upright spring treatment in order to reduce the patient's inadaptability.

In summation of the description above, the long-arm type upright molar tooth spring of the invention has unique and innovative features and breaks through the traditional way of using an elastic ring or a brass wire and overcomes the shortcomings of the prior art that is time-consuming and ineffective. Compared with the prior art, the present invention has the following advantages: (1) The application is more convenient; (2) The spring will not damage the patient's tissues; (3) The invention provides a modified molar tooth upright spring with the same effect. Obviously, the present invention herein enhances the performance than the conventional structure and further complies with the patent application requirements and is duly filed for patent application.

While the invention has been described by means of specific embodiments, numerous modifications and variations could be made thereto by those skilled in the art without departing from the scope and spirit of the invention set forth in the claims.

What is claimed is:

1. A long-arm type upright molar tooth spring, for uprighting an impacted second molar tooth, comprising:

a lingual groove rest, for securing one end of the tooth spring in at a lingual groove of a first molar tooth;

a loop, adjacent to said lingual groove rest, having a length spanning from the lingual groove of the first molar tooth to a marginal distance below the highest point of the profile of the mesial side of the impacted second molar tooth, and a width spanning from the lingual side of the first molar tooth to the buccal side of the first molar tooth, wherein the loop includes a body having at least one contact end which extends to and directly contacts the wall of the impacted second molar tooth adjacent to the first molar tooth;

a buccal bracket rest, adjacent to said loop, for resting the long-arm type upright molar tooth spring at a buccal bracket of the first molar tooth;

a reactivating area, adjacent to said buccal bracket rest;
a lever, adjacent to said reactivating area, for applying a force onto the second molar tooth; and
an end arc, adjacent to said lever.

2. The long-arm type upright molar tooth spring of claim 1, wherein the body further comprises a plurality of contact ends, and the contact ends are coupled to the body.

3. The long-arm type upright molar tooth spring of claim 1, wherein the arc body further comprises a plurality of contact ends, and the contact ends are integrally formed with the body.

4. A long-arm type upright molar tooth spring, for uprighting an impacted second molar tooth, comprising:
a lingual groove rest, for resting the tooth spring in a lingual groove of a first molar tooth;
a loop, adjacent to said lingual groove rest, having a length spanning from the lingual groove of the first molar tooth to a mar inal distance below the highest point of the profile of the mesial side of the impacted second molar tooth, and a width spanning from the lingual side of the first molar tooth to the buccal side of the first molar tooth;
wherein the loop includes a body, having at least one contact end which extends to and directly contacts the wall of the impacted second molar tooth adjacent to the first molar tooth;
an elongated contact structure, coupled to said loop;
a buccal bracket rest, adjacent to said loop, for resting the long-arm type upright molar tooth spring at a buccal bracket of the first molar tooth;
a reactivating area, adjacent to said buccal bracket rest;
a lever, for applying a force onto the second molar tooth; and
an end arc.

* * * * *